United States Patent
Wroblewski et al.

(10) Patent No.: US 10,202,843 B2
(45) Date of Patent: Feb. 12, 2019

(54) MEASURING SETTLING IN FLUID MIXTURES

(71) Applicant: STATOIL PETROLEUM AS, Stavanger (NO)

(72) Inventors: Tomasz Wroblewski, Stavanger (NO); Lorents Reinås, Stavanger (NO); Tor Henry Omland, Stavanger (NO); Stian Mjølhus, Stavanger (NO)

(73) Assignee: STATOIL PETROLEUM AS, Stavanger (NO)

( * ) Notice: Subject to any disclaimer, the term of this patent is extended or adjusted under 35 U.S.C. 154(b) by 95 days.

(21) Appl. No.: 14/764,029

(22) PCT Filed: Jan. 29, 2013

(86) PCT No.: PCT/EP2013/051668
§ 371 (c)(1),
(2) Date: Jul. 28, 2015

(87) PCT Pub. No.: WO2014/117812
PCT Pub. Date: Aug. 7, 2014

(65) Prior Publication Data
US 2015/0354343 A1    Dec. 10, 2015

(51) Int. Cl.
*E21B 47/10* (2012.01)
*G01N 15/04* (2006.01)
(Continued)

(52) U.S. Cl.
CPC ............. *E21B 47/10* (2013.01); *G01N 15/04* (2013.01); *G01N 29/024* (2013.01);
(Continued)

(58) Field of Classification Search
CPC ...... E21B 47/10; G01N 15/04; G01N 29/024; G01N 29/028; G01N 2015/0053;
(Continued)

(56) References Cited

U.S. PATENT DOCUMENTS 3,648,513 A * 3/1972 Patterson ................ E21B 43/28
181/102
3,896,660 A * 7/1975 Valentyik ............... G01N 15/04
73/438
(Continued)

FOREIGN PATENT DOCUMENTS

JP          58019557 A  *  2/1983   ........... G01N 29/024

OTHER PUBLICATIONS

Tor Henry Omland "Particle settling in non-Newtonian drilling fluids" Stavanger : University of Stavanger, Faculty of Science and Technology, Department of Petroleum Engineering 2009 (PhD thesis UiS, No. 80).*
(Continued)

*Primary Examiner* — John Fitzgerald
(74) *Attorney, Agent, or Firm* — Birch, Stewart, Kolasch & Birch, LLP (57) ABSTRACT

A method and apparatus for measuring a property of settling of a first phase in a second fluid phase of a mixture. In order to measure the property of settling, the mixture may be contained in a chamber, an acoustic wave may be repeatedly passed vertically through the mixture, a transit time may be measured for each acoustic wave to traverse the mixture, and the property of settling using a change in the transit times of the acoustic waves may then be determined. In various embodiments, the property of settling can be a degree of settling.

21 Claims, 8 Drawing Sheets (51) Int. Cl.
  *G01N 29/028* (2006.01)
  *G01N 29/024* (2006.01)
  *G01N 15/00* (2006.01)

(52) U.S. Cl.
  CPC ... *G01N 29/028* (2013.01); *G01N 2015/0053* (2013.01); *G01N 2291/022* (2013.01); *G01N 2291/028* (2013.01); *G01N 2291/02416* (2013.01); *G01N 2291/048* (2013.01)

(58) Field of Classification Search
  CPC ... G01N 2291/02416; G01N 2291/022; G01N 2291/028; G01N 2291/048
  USPC .......... 73/152.18, 61.62–61.68, 61.45, 64.53
  See application file for complete search history.

(56) References Cited

U.S. PATENT DOCUMENTS

| | | | | |
|---|---|---|---|---|
| 4,041,502 A * | 8/1977 | Williams | ........ | G01D 9/30 250/573 |
| 4,522,068 A * | 6/1985 | Smith | ........ | G01N 9/24 73/32 A |
| 4,718,269 A * | 1/1988 | Der Kinderen | ........ | G01F 1/663 73/19.03 |
| 4,746,421 A * | 5/1988 | Turbitt | ........ | B03B 5/623 209/158 |
| 4,754,839 A | 7/1988 | Gold et al. | | |
| 4,770,043 A * | 9/1988 | Cobb | ........ | G01N 29/024 73/32 A |
| H608 H | 3/1989 | Goolsby | | |
| 5,121,629 A * | 6/1992 | Alba | ........ | G01N 15/02 73/602 |
| 5,125,264 A | 6/1992 | Beuzard et al. | | |
| 5,616,856 A * | 4/1997 | Castel | ........ | G01F 23/2962 73/61.44 |
| 5,616,872 A * | 4/1997 | O'Brien | ........ | G01N 15/0266 324/453 |
| 5,661,237 A * | 8/1997 | Dussan V. | ........ | E21B 47/102 324/324 |
| 5,763,776 A * | 6/1998 | Birch | ........ | G01F 23/02 116/216 |
| 5,939,622 A * | 8/1999 | Fay | ........ | G01F 23/296 73/61.63 |
| 5,992,223 A | 11/1999 | Sabins et al. | | |
| 6,128,949 A * | 10/2000 | Kleinberg | ........ | G01N 33/2823 166/250.01 |
| 6,560,548 B1 * | 5/2003 | Roudil | ........ | G01N 29/024 702/103 |
| 6,584,833 B1 * | 7/2003 | Jamison | ........ | E21B 49/005 73/54.28 |
| 6,612,156 B1 * | 9/2003 | Hakimuddin | ........ | B01F 3/1242 73/597 |
| 7,010,979 B2 * | 3/2006 | Scott | ........ | G01N 15/02 73/596 |
| 7,096,719 B2 * | 8/2006 | Gysling | ........ | G01F 1/667 73/19.03 |
| 7,140,239 B2 * | 11/2006 | Greenwood | ........ | G01N 15/04 73/53.03 |
| 7,454,958 B2 * | 11/2008 | Ellson | ........ | B01L 3/0268 73/54.02 |
| 7,615,954 B1 * | 11/2009 | Potter | ........ | G01F 23/296 318/291 |
| 9,719,965 B2 * | 8/2017 | Mandal | ........ | G01N 29/02 |
| 2003/0033866 A1 * | 2/2003 | Diakonov | ........ | E21B 49/081 73/152.55 |
| 2003/0150262 A1 * | 8/2003 | Han | ........ | E21B 47/101 73/152.18 |
| 2003/0164038 A1 * | 9/2003 | Han | ........ | E21B 47/101 73/152.58 |
| 2004/0139792 A1 * | 7/2004 | Cobb | ........ | G01N 29/032 73/61.75 |
| 2004/0182138 A1 | 9/2004 | Greenwood et al. | | |
| 2005/0262936 A1 * | 12/2005 | DiFoggio | ........ | G01V 8/02 73/152.18 |
| 2006/0272815 A1 * | 12/2006 | Jones | ........ | C09K 8/36 166/278 |
| 2007/0035738 A1 * | 2/2007 | Bordelon | ........ | G01N 15/0227 356/442 |
| 2011/0167901 A1 * | 7/2011 | Jamison | ........ | G01N 9/00 73/152.18 |
| 2011/0209558 A1 * | 9/2011 | Sugiura | ........ | G01F 1/662 73/861.18 |

OTHER PUBLICATIONS

International Search Report issued in PCT/EP2013/051668, dated Oct. 29, 2013.

Omland et al., "Detection Techniques Determining Weighting Material Sag in Drilling Fluid and Relationship to Rheology", Annual Transactions of the Nordic Rheology Society, vol. 15, 2007, 9 pages.

Written Opinion issued in PCT/EP2013/051668, dated Oct. 29, 2013.

\* cited by examiner

MEASURING SETTLING IN FLUID MIXTURES

TECHNICAL FIELD

The invention relates to phase separation, and, in particular, to measuring a property of settling in fluid mixtures. In certain embodiments, it relates to measuring particle settling in a drilling fluid.

BACKGROUND

Fluid mixtures with two or more phases are handled in fluid systems in a wide range of industries. Such mixtures can include emulsions, solutions and particle suspensions or the like and may be moved or circulated through various flow spaces or conduits in such systems. Dependent on conditions and phase types, the mixtures may display a separation of phases and a tendency of one of the phases settling within another phase. This may be seen particularly if the fluids are at rest, poorly mixed or moving slowly in conduits. It can be important to handle the mixtures in such a way as to restrict or avoid settling. For example, it may be desirable to avoid a build up of residues or blockages in conduits. This may require knowledge of the behaviour of the fluid mixture with regard to settling, for example to allow appropriate constituents of the fluid to be selected. For example, in a mixture where a first insoluble phase constitutes particles within a fluid second phase, an appropriate amount or type of particles and fluid may be selected.

The term "settling" includes settling by sinking or rising of one phase within another phase.

The issue of settling is a particular concern in wellbore drilling operations, for example in the oil and gas industry, where drilling fluid is circulated through a well bore. The drilling fluid is pumped from a surface rig into the well through a drill string provided with a drill bit at its lowermost end for penetrating the subsurface rock formations. The fluid exits the drill string near the drill bit, and passes back up through the well to the surface rig in an annular space between an outer surface of the drill string and a wall of the wellbore.

The drilling fluid acts to lubricate the drill string, cool the drill bit and transport drill cuttings out of the well bore. In addition, it may be needed to seal permeable formations traversed by the wellbore. A sufficient hydrostatic pressure is also required in the well in particular to prevent gas, water or oil leaking into the well. The drilling fluid needs to have an appropriate composition in order to fulfil these functions.

In particular, in order to provide the hydrostatic pressure required, it is usual to increase the density of the drilling fluid, whether it be water or oil based, by adding insoluble particles to serve as weighting agents. Typically, barite particles are used.

Performance of a drilling operation depends on the particles staying suspended within the drilling fluid. This is usually achieved whilst circulating drilling fluid through the well. However, it is unavoidable that circulation is halted from time to time during a drilling operation. At such times, the insoluble particles will tend to settle in the fluid, out of suspension. For example, the drilling fluid may exhibit particle "sag" where settling particles fail to follow the circulation of the drilling fluid out of the wellbore. This can result in fluctuations in density of the drilling fluid exiting the well bore during an operation. Sag can be thought of as a settling of solid materials in a fluid owing to gravitational effects. Barite sag is described as the segregation of weighting material due to gravitational effects which can lead to density variations in drilling fluids. The problem can also occur with other high density weighting agents used to increase density, such as hematite. Barite sag is almost always characterized by drilling fluids having a density below nominal (surface) mud weight, followed by density above nominal when circulating bottoms-up after a trip.

There are various different mechanisms for sag, any of which can be in operation. These can be summarized as:

Static settling, owing to gravitational effects;

Dynamic settling, most common during slow pumping or movement of the fluid, and more severe than static sag; and Slumping, owing to the Boycott effect, in which an inclined tube containing particles in a suspending fluid sets up an internal flow that is similar to convective flow in enclosed spaces subject to a lateral temperature gradient. As the settling particles migrate to one side of the inclined tube, the resulting density variation creates a pressure variation across the tube with a pressure gradient component that induces convective flow. The Boycott effect is therefore observed in inclined wells. If the settling of particles progresses far enough, or settling behaviour is not adequately taken into account, it can cause severe operational problems such as well instability, well kick, stuck-pipe, loss of circulation, problems with running a casing or liner and loss of the fluid column weight (a drop in hydrostatic pressure) which can lead to unwanted gas or oil influx into the well which, in severe cases, can cause a blowout.

It is therefore particularly desirable to understand the drilling fluid quality during wellbore operations, so that operators can respond appropriately, for example to adjust procedures to reduce periods of no circulation or to change the composition of the drilling fluid. During the fluid design phase, typically performed in a laboratory, it is also essential to understand and quantify a degree to which various fluids are prone to sag in order to provide the most optimum fluid solution prior to field application.

Measurements may therefore be performed on the drilling fluid as it is pumped into or exits the well bore, providing an indication of whether the drilling fluid being used is suitable. In particular, "condition monitoring" is applied during drilling operations whereby repeated tests are performed on the drilling fluid to define a drilling fluid signature characterising the instantaneous state of the drilling fluid and/or of the well bore. A signature may be defined by a combination of numerous types of measurement performed on the drilling fluid. If the signature changes, it is an indication that the drilling fluid or wellbore state has changed. Knowing the current settling performance of a drilling fluid is an important indicator to take into account of and a key in avoiding operational problems particularly when the drilling fluid stands still over a period of time.

However, there is currently a lack of simple but reliable measurement for determining particle settling properties in drilling fluid. In particular, there is a lack of a good technique that is suitable for use in the field.

Note that, while the above description refers to the desire to keep a solid phase in suspension in a fluid, other applications may require a high degree of settling. For example, it may be required to use settling to segregate a solid phase from a liquid phase. In this case, it is also important to measure the settling properties of solid particles in a liquid, or settling properties of different liquid phases in an emulsion.

At present, there is often used a static sag test based on density measurements to provide an indication of settling behaviour. This technique involves taking a sample of drilling fluid, and then letting the particles settle within the fluid. Then, a discrete measurement of the density of an upper part and lower part of the sample mixture is made. The density measurements are combined for example as a ratio to give a numerical value or "sag factor" which is used as an indicator of particle sag. A measurement of density is made at the upper and lower parts once the settling has occurred. No information is provided on how settling progresses and the accuracy of results using this approach can be relatively poor.

Alternatively, dynamic measurement techniques may be used which take into account shear effects. For example, direct weight measurements can be made which take into account rotation and shear rate effects of particles, temperature, vibrations and fluid compositional measurements. To the knowledge of the inventors only a single example of direct weight measurement equipment is available for use currently, set up in an onshore laboratory. It is not suited to field use. Sag flow loop tests can be performed involving putting fluid to be measured into motion in a flow loop taking into account wellbore angle effects. This requires large and relatively complex measurement equipment.

Nuclear Magnetic Resonance (NMR) and viscometer testing are other potential methods.

Acoustic measurement techniques have also been proposed for characterising settling in fluid mixtures. Developments of these acoustic techniques are typically focused upon perfecting measurements transverse to the settling direction. Thus, transmission and detection of an acoustic signal occurs on a path along which the particle volume fraction or distribution of particles is substantially uniform. Upon settling under the influence of gravity, particles tend to move through the mixture in or parallel to the direction of gravity, substantially vertically, and then settle forming a layer of particles in the mixture. Existing techniques may use horizontal detection arrangements, across the settling direction, to target a region where the particle volume fraction is uniform.

The document US2004/00182138 describes a system for determining properties of settling suspensions. It refers to use of a supplementary transducer which operates in a vertical direction. The transducer is limited to detecting echo effects from particles in the suspension.

SUMMARY

According to a first aspect of the invention therefore, there is provided method of measuring a property of settling of a first phase in a second fluid phase of a mixture. The method includes the following steps:
  a. contain the mixture in a chamber;
  b. repeatedly pass an acoustic wave vertically through the mixture;
  c. measure a transit time for each acoustic wave to traverse the mixture; and
  d. determine the property of settling using a change in the transit times of the acoustic waves.

As an option, the property of settling is an occurrence of settling.

The property of settling is optionally a degree of settling, in which case the determining step comprises estimating the degree of settling using the change in the transit times of the acoustic waves.

The step of estimating the degree of settling optionally includes comparing the measured transit time with known transit times for a similar mixture under similar conditions to estimate a degree of settling of the first phase in the second fluid phase.

The step of estimating the degree of settling includes optionally correlating the change in the transit times with the degree of settling according to an empirical correlation relationship derived from historical test results or observations.

Embodiments may include the steps of estimating values of acoustic impedance of the mixture from the measured transit times, and determining the property of settling using the values of acoustic impedance.

Embodiments optionally include the steps of measuring an amplitude for each of the acoustic waves, and determining the property of settling using a change in the amplitudes. In this case, a further option is to compare the measured amplitude with a reference amplitude to determine an amplitude attenuation for each of the acoustic waves, and determine the property of settling using a change in the attenuation of amplitudes.

As an option, the temperature and/or pressure of the mixture is controlled. This allows the test to simulate real-work conditions.

As an option, the first phase comprises insoluble solid particles, and the estimate of the degree of settling is used as an estimate of settling of solid particles in the second fluid phase. As an alternative option, the mixture comprises an emulsion, wherein the first phase comprises a fluid phase that is immiscible in the second fluid phase, wherein the estimate of the degree of settling is used as an estimate of emulsion stability. As a further alternative option, the mixture is a saline mixture, wherein the first phase comprises a salt insoluble in or precipitated from the second fluid phase, wherein the degree of settling of the salt is used as an estimate of salinity or salt saturation.

The mixture may include a third phase comprising insoluble solid particles.

As an option, the property of settling is sag, and the method includes repeating the steps a. to d. for different mixtures, and estimating sag by comparing the determined property of settling of a first mixture with the determined property of settling of a second mixture.

As a further option, the method allows the performance of steps a, b and c in real-time during a drilling operation. This allows measurements to be made directly and minimizes disruption to drilling operations.

According to a second aspect of the invention, there is provided an apparatus for measuring a property of settling of a first phase in a second fluid phase of a mixture. The apparatus is provided with a chamber arranged to receive a sample of the mixture, a source of acoustic waves arranged to repeatedly pass acoustic waves vertically through the mixture, a sensor for detecting the acoustic waves, means for determining a transit time for each acoustic wave to traverse the mixture, and means for determining the property of settling using the change in the transit times of the acoustic waves.

As an option, the apparatus further comprises means for comparing the measured transit time with known transit times for a similar mixture under similar conditions to estimate a property of settling of the first phase in the second fluid phase. The means for comparing the measured transit time with known transit times for a similar mixture under similar conditions optionally comprises a processor and a database of previously obtained data.

As an option, the apparatus includes processing means for processing measured times for determining the property of settling.

The sensor is optionally arranged to detect an amplitude for each acoustic wave, and the apparatus has means for determining the property of settling using the detected amplitudes.

The chamber optionally has a transparent window for viewing the mixture. As a further option, the chamber is provided with a back light for illuminating the mixture contained in the chamber for facilitating viewing.

According to a third aspect of the invention, there is provided a computer program for processing data comprising transit times of detected acoustic waves passed vertically through a mixture contained in a chamber, and determining a property of settling of a first phase in a second fluid phase of the mixture using the transit times.

According to a fourth aspect of the invention, there is provided a computer comprising processing means for executing the computer program of the third aspect of the invention for determining the property of settling

BRIEF DESCRIPTION OF THE DRAWINGS

There will now be described by way of example only, embodiments of the invention with reference to the accompanying drawings, in which.

DETAILED DESCRIPTION

Figure 1:
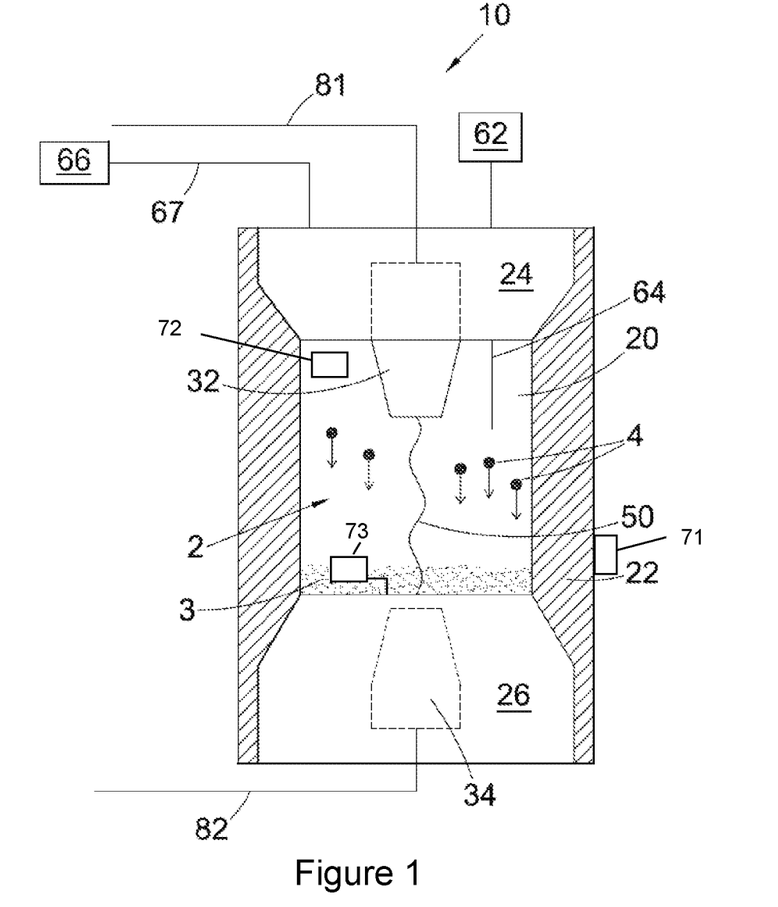
FIG. 1 is a cross-sectional representation of an ultrasonic drilling fluid analyser according to an embodiment of the present invention.

Turning firstly to FIG. 1, there is shown an analyser 10 for measuring a behaviour or property of settling of particles in a fluid such as a drilling fluid. Such an analyser 10 may be used on a drilling rig. A sample of the drilling fluid being circulated through the well may be taken, located into and measured by the analyser 10. The drilling fluid analyser may also be used in onshore contexts, to measure an actual drilling fluid taken from the field, or to measure a synthetic drilling fluid sample for example to test new drilling fluid mixtures. The drilling fluid may be an oil-based fluid or a water-based fluid containing insoluble particles, typically barite particles which may have been added to the drilling fluid as a weighting agent. Note that while the description below concentrates on measuring settling properties of a drilling fluid, the methods described may also be used to measure the settling properties of other types of fluid that have a solid phase in suspension or a liquid phase in an emulsion. Note also that for a drilling fluid, which typically contains solid particles suspended in a liquid phase, the term "sag" is used to describe settling of the solid phase due to gravitational effects, as described above.

In terms of construction, the analyser 10 has a test chamber 20 in which a volume of sampled drilling fluid 2 is received and contained. The test chamber is defined by a main body 22 and top and bottom lids 24, 26. Dimensions are relatively small with the volume of sampled fluid being around 250 ml and a distance between internal walls of the main body in the region of around 2 to 3 inches.

The settling properties of particles in the drilling fluid are determined by measuring the sampled drilling fluid 2 contained in the analyser 10. To do this, the analyser 10 has a transmitting acoustic transducer 32 fitted to the top lid 24 and a receiving acoustic transducer 34 fitted to the bottom lid 26. The transmitting transducer 32 is arranged to transmit an acoustic wave 50 (such as an ultrasonic pressure wave) through the test chamber 20 vertically through the sampled drilling fluid 2. The receiving transducer 34 is arranged to detect the pressure wave passed through the fluid 2. Pressure waves are passed through the chamber repeatedly throughout a test period during which settling occurs. Typically, the pressure waves are transmitted as discrete pulses. The interval between pulses may be selectable and chosen to minimise agitation of the fluid by the acoustic pulses so as to minimise the effect that they have on the rate of settling in the mixture. The longer the interval between pulses, the lesser the vibration effect upon settling. The travel time of the pressure waves is measured and recorded. The travel time of the pressure waves differs in dependence upon the progress of settling of particles, and can provide a basis for detecting settling and estimating a degree of settling of particles in the drilling fluid, as explained in more detail below.

The drilling fluid analyser 10 includes a temperature controller 62 and temperature sensor 64 to keep the temperature consistent during measurement of the drilling fluid. For example, the temperature during measurement may replicate a wellbore temperature. The apparatus 10 may have a cooling or heating fluid supplied to it for cooling or heating the chamber if required. The cooling or heating fluid may be stored in a separate fluid bath (not shown) coupled to the apparatus. The temperature controller 62 may be programmed to heat or cool the chamber and control supply of heating or cooling fluid to the apparatus for temperature control. The controller may control the temperature in response to measurements of temperature inside the chamber performed by the temperature sensor 64. Thus, the controller may receive a temperature measurement signal from the sensor 64 and may initiate heating if the temperature measurement is lower than a desired temperature threshold value, and vice versa with regard to cooling. Alternatively, a heating element may be used instead of using a supply of cooling or heating fluid. In another alternative, the temperature may be measured using the sensor 64 and simply recorded using the controller during measurements.

In addition, the chamber can be pressurised for example so that the pressure of the sampled drilling fluid is representative of a well pressure. The analyser 10 is provided with a pressurised liquid flow applied to the chamber to pressurise the drilling fluid appropriately. A pressure controller 66 controls the supply of the pressurised liquid to the apparatus 10 via conduit 67. The pressure controller may be provided with a supply of water and air which is compressed to drive the water stream. The water stream exerts a pressurising force against one or both of the chamber lids 24, 26 to pressurise the drilling fluid sample 2 within the chamber. Typically, the pressure is controlled so that it remains constant during measurements.

In one embodiment, the drilling fluid analyser 10 may be implemented by adapting an ultrasonic cement analyser (UCA) device for use with drilling fluid. A suitable candidate for adaption is the model UCA 220 V-50 Hz which has an ultrasound operating frequency of 400 kHz, and provides pressurisation up to 20 000 psi marketed and supplied by Chandler Engineering and others, as described for example in U.S. Pat. No. 5,992,223, relevant parts incorporated herein by reference.

Figure 2:
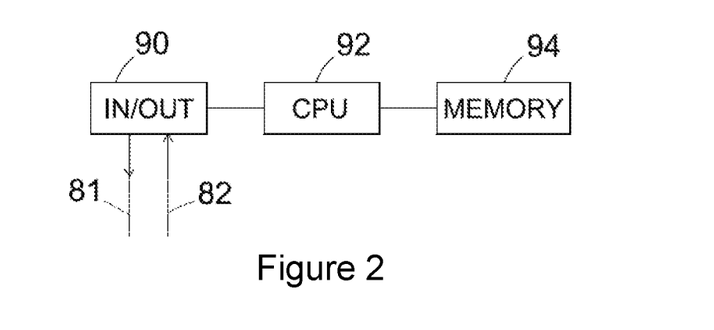
FIG. 2 is a schematic block diagram of a control system for controlling the drilling fluid analyser of FIG. 1.

In practice, the measurements by the analyser 10 are controlled and processed by a control system. A control system similar to that described in U.S. Pat. No. 5,992,223 may be applied, although adapted for use with drilling fluid measurements. Typically, the control system includes an in/out module 90, a processor 92 and a computer readable medium in the form of a memory module 94, as seen in FIG. 2. The in/out module 90 may provide and receive electronic data signals from the transducers via data lines 81, 82, and may include control electronics operable for example to initiate a pressure pulse in response to a command from the processor 92. The control electronics may also assist with temperature and pressure control. The signal transmitted to the transmitting transducer may define a shape and frequency of pressure waves, for example it may define a limited duration pressure pulse to be transmitted through the fluid. A receiving signal containing detected drilling fluid acoustic data is received by the control system from the receiving transducer 34 via a line 82. The control electronics may apply signal processing filters to the signal before the data are processed in other modules.

The processor 92 is controlled by and arranged to execute one or more computer programs stored on the memory module 94. There may be provided a computer program for perform logging and recording the drilling fluid data and/or for processing of data into a desired form, for example calculating travel times. The processing of data include performing a signal processing correlation by which transmitted and received data signals are compared in order to determine drilling fluid travel times. The memory module may otherwise serve to store measurement data, and may comprise a portable data storage device such as an optical disk.

It will be appreciated that the control system may be a distributed system functionally and physically. Thus, any one or more of the components 90, 92, 94 may be located on different devices, over a network. Similarly, different programs may be performed on different devices in different locations, and data may be stored in a plurality of memory modules on different devices in different locations. Conversely, the control system for the analyser 10 may be implemented on a computer, containing the necessary memory and computer programs, and/or in/out modules in a more centralised fashion.

The chamber 20 may have a transparent window 71 in order to visually observe the progress of settling of particles in the drilling fluid 2 from outside the chamber 20. The window may have a scale bar or ruler to facilitate measuring spatial indicators of progress of settling, such as the thickness of a layer of settled particles at the bottom of the fluid in the chamber. As a further option, the chamber is provided with a back light 72 for illuminating the mixture contained in the chamber for facilitating viewing.

The chamber may be provided with backlighting to help identify progress of settling and formation of layers in the fluid of contrasting particle volume fraction. Such observations may help to determine the duration of the test period or when to stop the measurements.

In certain variants, the acoustic measurements would be performed for a full settling period i.e., from an initial well mixed condition of the fluid until there are no changes in travel times and the solid particles have settled to a maximum extent. In the field, it is envisaged that a test period duration would be in the order of around 20-60 minutes. Thus, it may not be feasible or necessary to measure the travel times for a full settling period.

The drilling fluid analyser may also be provided with a mixing arrangement (not shown) for agitating the mixture prior to making the acoustic measurements. The mixing arrangement may include a paddle 73 provided for example in a bottom end of the chamber 20. Thus, the sampled mixture can be kept well mixed until the user wishes to perform the measurement of settling.

Figure 3A:
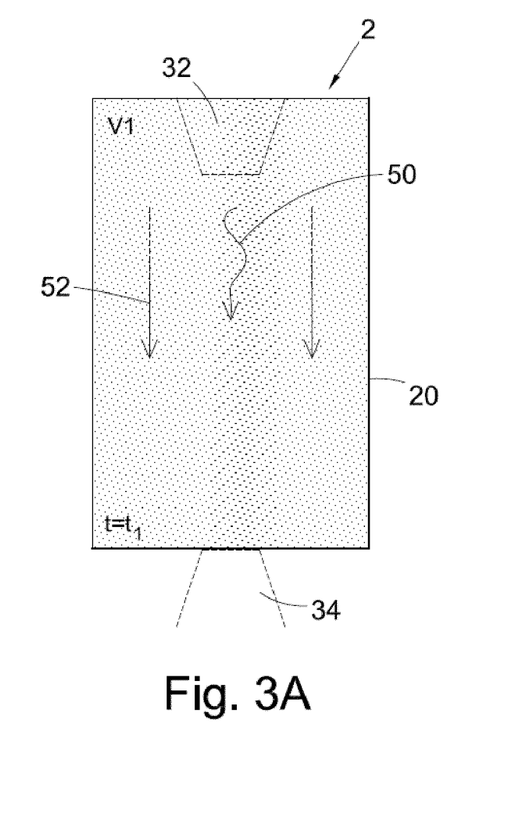
FIGS. 3A and 3B are schematic representations of the fluid chamber of the drilling fluid analyser of FIG. 1, showing distribution of particles during settling at a first time $t_1$ and a second time $t_2$.
Figure 3B:
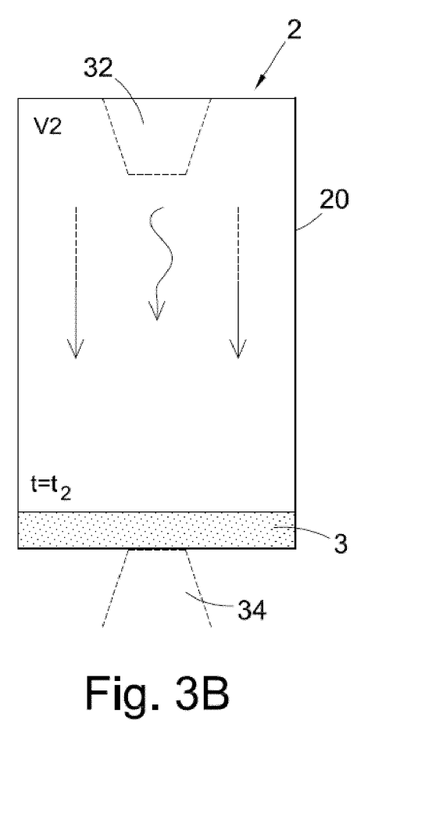

With reference now to FIGS. 3A and 3B, the basis for measuring a degree of particle settling is described in more detail. In these figures, volumes of the sampled drilling fluid 2 contained in the test chamber 20 are shown at different times during a test period. In FIG. 3A, at a time $t_1$, the particles are well mixed throughout the volume of fluid 2, and practically no settling has occurred. At a later time $t_2$, the particles in the fluid have settled at a bottom end 27 of the chamber, forming a layer of particles.

Arrows 52 indicate the direction of settling of particles under the influence of gravity, and it can be seen that the acoustic waves 50 (which are typically ultrasonic waves but may be of any suitable frequency) are transmitted in the direction of settling, i.e. substantially vertically. The travel time of the acoustic waves across the chamber is measured. The travel time through the volume in FIG. 3A differs significantly from that of FIG. 3B in which particles have settled to a greater extent. More specifically, the time of travel in FIG. 3B is greater than in FIG. 3A. The speed of the acoustic wave through the mixture depends upon the properties of the medium, such as its acoustic velocity, and it can be seen that the build up of a layer at the bottom of the volume upon settling of the particles causes the travel time to increase. In the mixture of 3B there are effectively two acoustic velocities, one associated with the layer of particles and another with the region above the layer, whilst in 3A, the mixture has effectively a single velocity. The increase in travel time indicates therefore that the velocity of mixture in FIG. 3A does not equate to a simple sum of the velocities of the layered structure formed in FIG. 3B.

Figure 4:
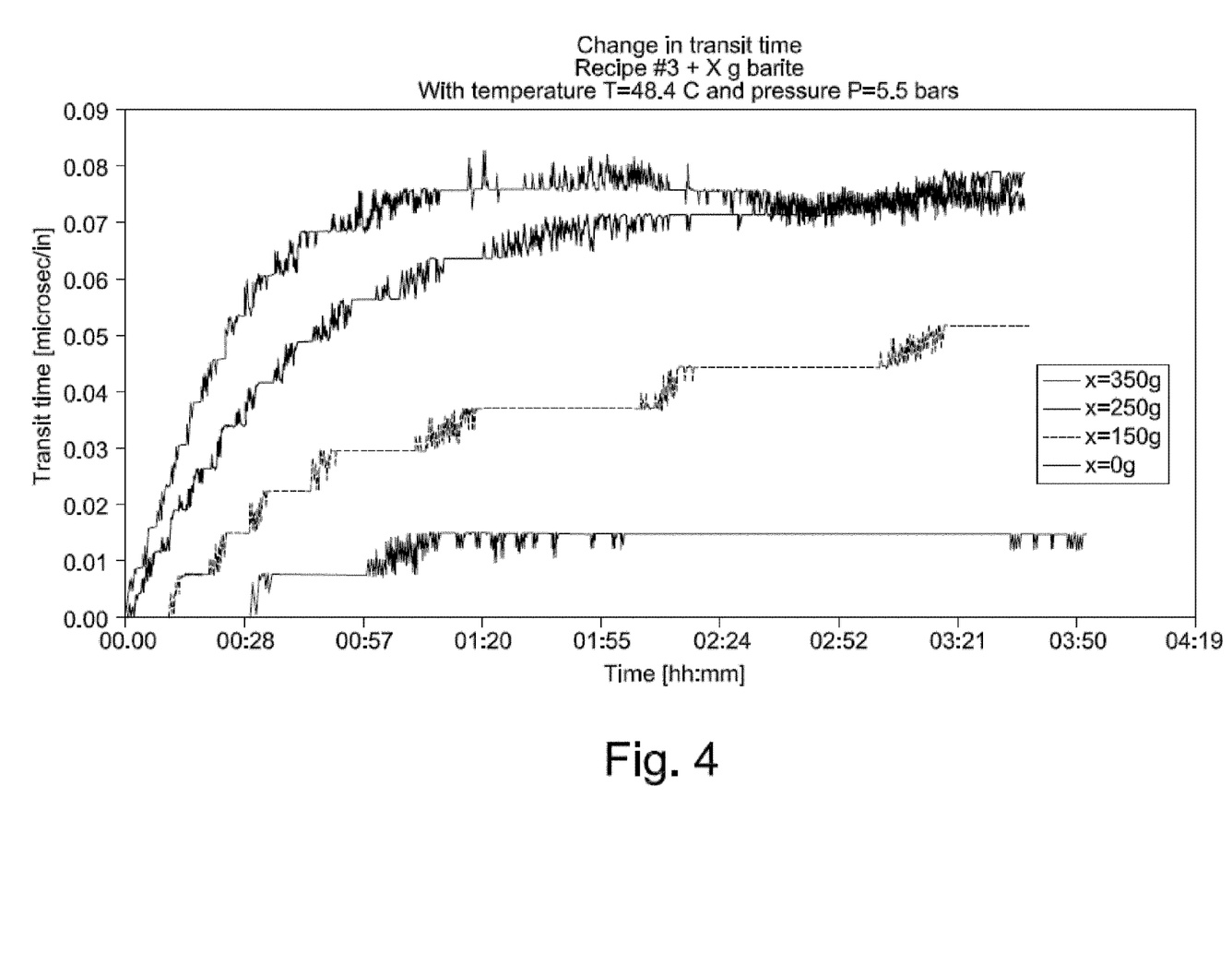
FIG. 4 is a graph of change in acoustic signal transit time against settling time for an oil-based drilling fluid.
Figure 5:
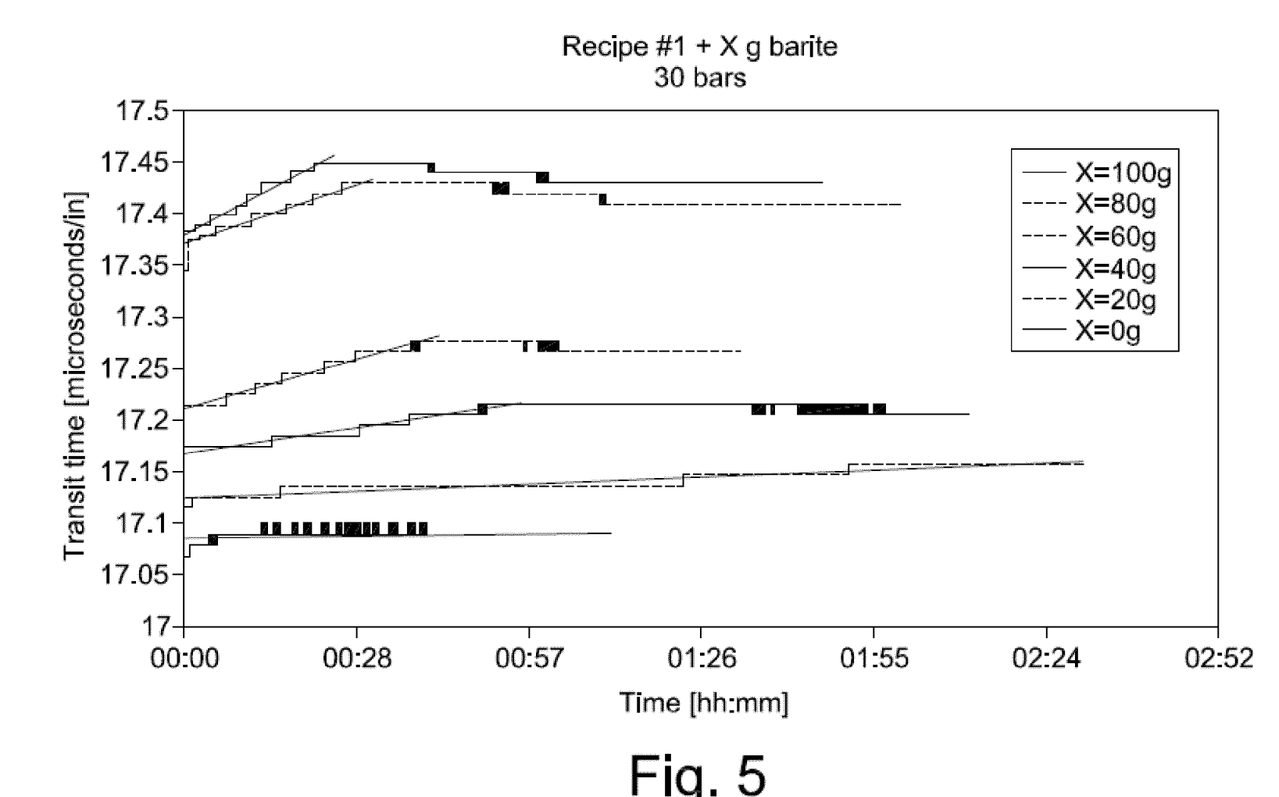
FIG. 5 is a graph of acoustic signal transit time against settling time for a water-based drilling fluid.

This settling behaviour for different experimental fluid mixtures is shown in the graphs of FIGS. 4 and 5. FIG. 4 shows variation in travel time during a test period for an oil-based drilling fluid indicating a settling behaviour. FIG. 5 gives the same type of results for a water-based drilling fluid. The different curves provide results from measurements on simulated drilling fluid mixtures with progressively smaller quantities of insoluble particles for each curve from top to bottom.

The initial measurement at the far left of each curve is a measurement made just after stirring the mixture such that the particles are well mixed throughout the mixture. Toward the far right end, there is no change in travel time in most of the curves corresponding to where the solids have settled to a maximum extent. At intermediate times, there is a progressive increase in travel times toward the fully settled condition, whilst a gradual build up of the particle layer at the bottom of the chamber takes place.

Prior to settling, the volume fraction of particles in the mixture will be substantially uniform before any settling occurs. However, after settling under gravity, the volume fraction of particles in a volume at the top of the chamber will be substantially lower than the volume fraction of particles in a settled layer at the bottom of the chamber.

The following can be determined:
1) The measured difference in travel time at $t=t_1$ and $t=t_2$ indicates the amount of settling. Thus, the occurrence of settling can be detected from the vertical acoustic travel time measurements. If $t_2$ is the start of the process and $t_2$ is taken after the acoustic travel time has stabilized, the difference in travel time between $t_1$ and $t_2$ is related to the total amount of settling. Note that the gradient of the slope of travel time between $t_1$ and $t_2$ is indicative of the rate of settling.
2) The increase in travel time at intermediate times, during settling, indicates that a degree of settling can be detected. However, in general there is not a direct correspondence of the increase in travel time and the degree of settling. Thus, to determine the degree of settling, correspondence to the degree of settling is determined according to a predetermined correlation.
3) A different behaviour of the travel time curves for different mixtures indicates that different types of mixture settling behaviours can be distinguished. This may assist to distinguish between different types of drilling fluid mixtures. As above, to determine the type of mixture a correlation is provided between the travel time behaviour and type of mixture.

Thus, empirical correlations may be developed between the following parameters, in order to use the travel time measurements in practical applications:

| Parameter 1 | Parameter 2 |
|---|---|
| Change in travel time/gradient | Rate of settling |
| Curve shape/change in gradient/rate of development of curve | Type of mixture/settling behaviour |
| Full settling time | Type of mixture/settling behaviour |
| Change in curve shape/repeat testing | Change in type of mixture/particle sag |

Separate correlations may be provided for:
a. water based fluids
b. oil based fluids
c. specific density of the substances of the phases
d. viscosity
e. relative amount of particles
f. size distribution of particles
g. shape of particles
h. emulsions, including:
    oil in water emulsions
    water in oil emulsions
    any other emulsions
i. pressure
j. temperature
k. other slow varying parameters of the system.

In order to obtain an empirical correlation between the acoustic measurements and a settling property, results from previous experimental tests may be used to determine statistically reliable relationships. For example, tests on drilling fluid samples such as those of FIGS. 4 and 5 may be performed whilst the actual, true quantity or weight of the solid particles which have settled into a particle layer are measured to determine how much of the original quantity of particles have settled. This may be performed repeatedly throughout a test period to determine the relationship for different points along the travel time curve. Thus, values of the actual weight proportion of particles that have landed in the particle layer over time may be obtained. One such measuring technique has been suggested and described by Tor Henry Omland "Particle settling in non-Newtonian drilling fluids" Stavanger: University of Stavanger, Faculty of Science and Technology, Department of Petroleum Engineering 2009 (PhD thesis UiS, no. 80), relevant parts incorporated herein by reference. For a particular fluid/solid phase mixture, settling measurements obtained using a different technique can be compared to the acoustic measurements in order to allow future acoustic measurements to be used to give an indication of the settling properties of the mixture. Experimental results can be used to build up a library of data for different fluid mixtures at different conditions (such as temperature, concentration, pressure and so on)

This correlation may be stored in a database, for example on the memory module of the control system of the analyser, and looked up in order to determine whether there is a match with later measurement results. Thus, if the travel time curve of a mixture is measured and determined to match stored data, the appropriate relationship of change in travel time to amount of settling is applied as defined in the correlation, thereby indicating the amount of settling from the travel time data. The conversion of the travel time data may be carried out automatically by the analyser, such that the data that are processed may be in the form of the degree of settling rather than travel times.

The technique may also be used for condition monitoring in the field. For example, repeated sampling and measurement of the drilling fluid during well operations can be used to observe any changes in settling behaviour. Variations in the travel time curves which are outside of the normal variation expected by the controlled addition of particles, type of fluid or progression of drilling into new formations, may indicate different fluid mixtures and/or particle content which could be an indicator of sag or other operational problems.

It may be advantageous to convert the measurement data from the analyser into acoustic impedance values. The characteristic impedance of a medium is a material property, given generally by:

$$Z_0 = \rho \cdot c \quad \text{(Eq. 1)}$$

where
$Z_0$ is the characteristic acoustic impedance (N·s/m3)
$\rho$ is the density of the medium (kg/m3), and
$c$ is the longitudinal wave speed or sound speed (m/s)

A characteristic impedance value can thus be obtained by multiplying the velocity of the medium (reciprocal of the transit times) with a separate, "external" density measurement from the drilling fluid. Suitable density measurements are routinely taken on a drilling rig as part of the condition monitoring procedures. These may comprise measurements of the average density of the drilling fluid sample.

As drilling fluids are engineered to have a certain density by addition of solid particles, settling measurements or tests as described above are performed on drilling fluids with different or changing compositions over time. This means there can be relatively large differences in density from test to test due to the addition of particles. By processing the data using the computer program or by configuring the analyser to use the external density measurement and produce acoustic impedance values, it may allow one to characterise or better compare the same types of system where drilling fluids have a different density. The conversion to acoustic impedance is therefore effectively a normalisation to mask the effects of density on the measurements.

In addition, amplitudes of the acoustic waves may be detected at the receiving transducer 34 and measured using the analyser 10. The amplitudes are of particular interest for determining the attenuation of the acoustic signal as a function of distance through the sample. In this case, there is a fixed distance, such that where settling has occurred and a particle layer develops such as in FIG. 3B, a change in signal amplitude or attenuation can indicate that settling has occurred or can indicate a degree of settling, using correlations in a similar way to those described above when travel times are used. The use of transit times, acoustic impedance, and/or signal attenuation in combination provides additional information concerning particle settling and a basis for a better interpretation and correlation to actual settling measurements. A combination of transient time, acoustic impedance and signal attenuation may be particularly useful for developing good correlations and for determining a property of settling.

It should also be noted that the particles may have different properties when settled in a layer depending on particle size, shape, density, chemistry etc. Using the acoustic impedance and/or signal attenuation methods, an indication of "strength" of the settled layer may be obtained, for example indicating if particles are sticking together etc. For example, hydrophilic particles may tend to stick together whilst hydrophobic particles may tend to be easier to repel each other. In a well, this could give an indication of how easily a settled layer could wash away etc.

The ultrasound attenuation measurements can be arranged to give information about a fluid's extensional viscosity where the acoustic signal is transferred in a horizontal direction. Using the response in signal attenuation can also describe the settling tendency of particles in fluids.

The examples described above relate to the use of the analyser in the field, wherein a sample of a fluid is obtained from an oil well and tested to determine the degree of settling. However, in other embodiments it may be used in a laboratory onshore on synthetic or historical drilling fluids, in advance of performing drilling operations. The data may then be used to help design an oil well and a drilling fluid that has the required settling properties. It may also be used, for example, in quality control applications.

The analyser may also be used in other fields and on other types of fluid mixtures, where the detection of settling and degree of settling is advantageously determined.

For example, it can be used on emulsions and settling of an immiscible phase of the emulsion within another fluid phase, for example when an emulsion breaks down, i.e. to test emulsion stability. The immiscible phase may form a layer in the bottom of the chamber during the test.

Similarly, in a saline mixture where a salt has precipitated from a solution, the technique may detect precipitation, and indicate the degree of precipitation or test the temperature at which precipitation may occur. In a similar manner to the other embodiments described above, a layer of precipitated material may gradually form at the bottom of the test chamber occupying a greater volume fraction than it does in other parts of the mixture in the chamber.

It may also be noted that the fluid may have a plurality of settling phases within the fluid, for example where there are solid particles mixed with an emulsion. In this case, a three layer settling structure may occur within the fluid, with three associated acoustic velocities giving rise to travel time data which can be used in a similar manner to the examples described above to provide a measure of settling and/or emulsion stability.

It will be appreciated that the one of the phases will generally be lighter than the other. Thus, particles may be selected which are lighter than the second fluid phases such that they float. Particles may in this case settle by rising within the second phase and develop a layer of particles in an upper part of the mixture. Measurement of the occurrence and degree of settling can be performed in similar way to that described above.

A particular advantage of the technique described here is that measurements are performed while the fluid sample is static at well pressures and temperatures. This replicates closely the natural conditions of the well, in particular when drilling operations and well circulation has halted. Furthermore, measurements can be performed in "real-time" during drilling by taking a sample of the drilling fluid.

EXAMPLE

The following example is presented in order to illustrate an embodiment in which a curve such as one illustrated in FIG. 4 or 5 is used to estimate the degree of settling by empirically comparing it to settling measurements obtained in a different way.

Figure 6:
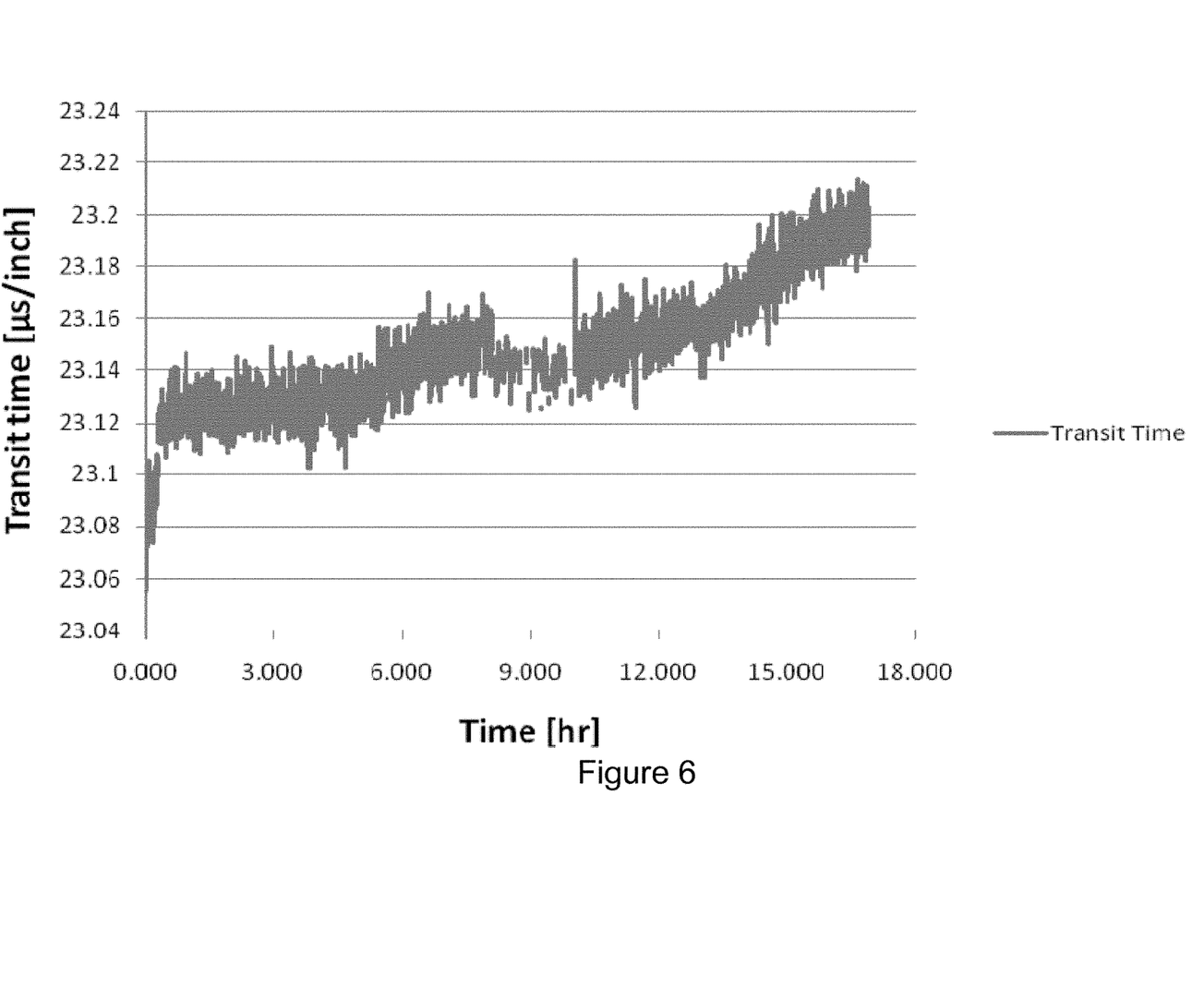
FIG. 6 is a graph of acoustic signal transit time against settling time for a drilling fluid.

A standard barite drilling fluid was prepared. FIG. 6 shows a graph of transit time with respect to time for the drilling fluid that is undergoing settling. As described above, the rate of settling can be related to the slope of the transit time curve. The steeper the slope, the greater the rate of settling. It can be seen that for the drilling fluid of FIG. 5, the rate of settling initially goes up rapidly, and then increases more slowly.

Figure 7:
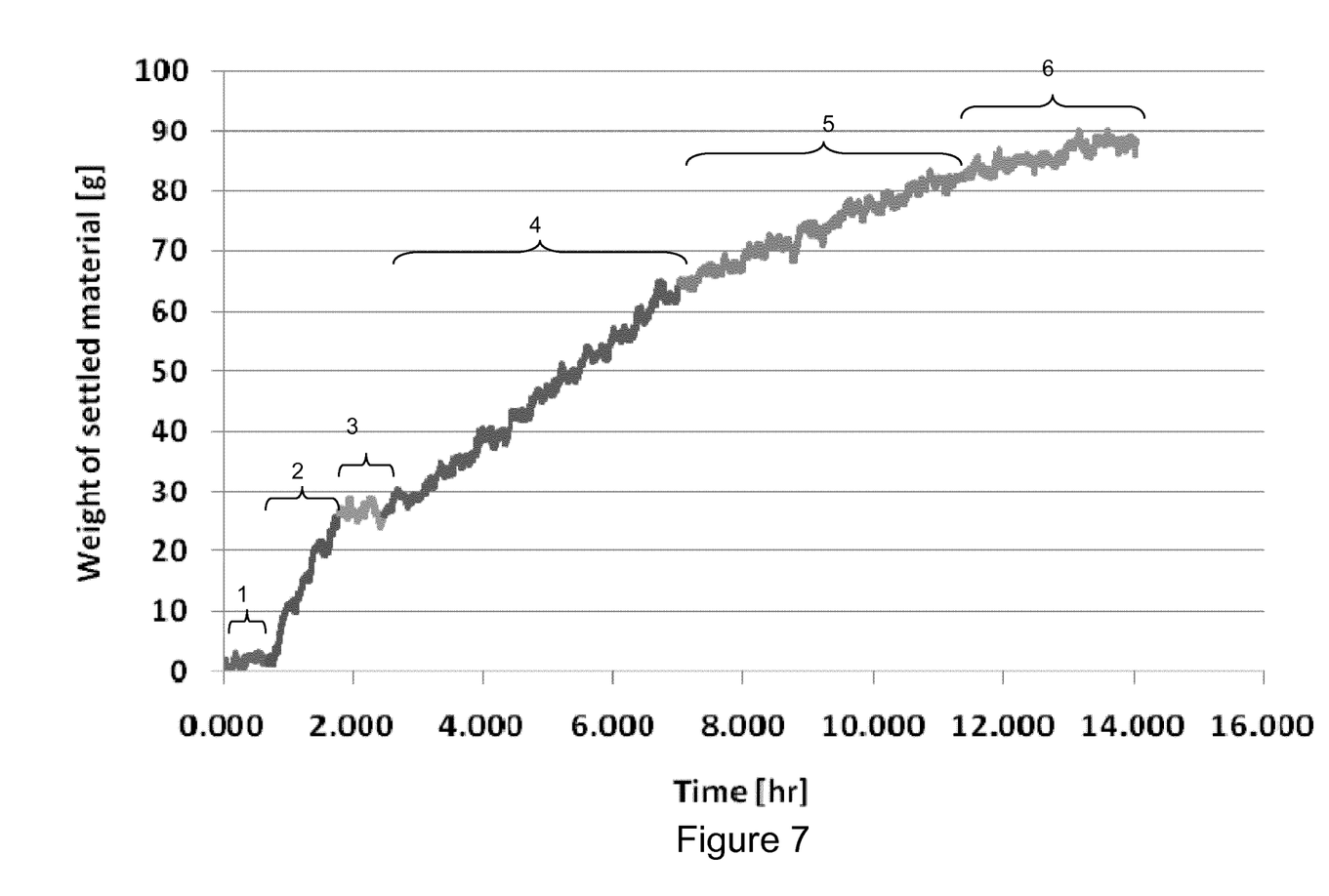
FIG. 7 is a graph of weight of settled material against settling time for the same drilling fluid as that shown in FIG. 6.

Turning now to FIG. 7, a chart showing the weight of settled material with respect to time for the same drilling fluid is illustrated. This uses a direct weight measurement, and is provided for comparative purposes only. It does not use transit times. In both FIGS. 5 and 6, it can be seen that an initial sudden increase is measured (this is delayed slightly for the direct weight measurement, as the material takes time to settle). The chart of FIG. 6 shows an initial steep slope followed by a shallower slope which then gradually becomes steeper. The chart of FIG. 7 on the other hand shows an initial steep slope followed by a shallower slope which then gradually becomes shallower. However, the results for the first few hours of testing are substantially the same.

In order to obtain an indicator for estimating settling velocity, a chart unification procedure must be carried out. The reason for this is that when the units on the X and Y axes of the graphs of FIGS. 6 and 7 are not in compliance, the settling velocity indicator cannot be calculated. As described above, the settling velocity can be estimated using the gradient of the slope of the graphs according to Equation 2:

$$y = ax + b \quad \text{(Eq. 2)}$$

where a is the gradient of the slope.

An exemplary technique for unifying axis units is presented below.

A share of reference time is calculated according to Equation 3 as follows:

$$Ts_i = \frac{T_i}{T_{ref}} \quad \text{(Eq. 3)}$$

where $Ts_i$ is the share of a reference time, $T_i$ is a time of measurement and $T_{ref}$ is a reference time.

Note also that a share of reference acoustic velocity or a share of acoustic impedance could be calculated and used similarly. To take the example of calculating a share of acoustic impedance, the specific acoustic impedance, Z, of an acoustic component (in N·s/m3) is the ratio of sound pressure p to particle velocity v at its connection point as shown in Equation 4:

$$Z = \frac{p}{v} = \frac{I}{v^2} = \frac{p^2}{I} \quad \text{(Eq. 4)}$$

where p is the sound pressure, $N/m^2$, v is the particle velocity, m/s, and I is the sound intensity, $W/m^2$. The acoustic impedance can therefore be calculated according to Equation 5 as follows:

$$Zs_i = \frac{Z_i}{Z_{ref}} \quad \text{(Eq. 5)}$$

Where $Zs_i$ is the share of reference impedance, $Z_i$ is the measured acoustic impedance and $Z_{ref}$ is the characteristic impedance of the medium (alternatively denoted $Z_0$), which is a material property and given by Equation 6:

$$Z_0 = \rho \cdot c \quad \text{(Eq. 6)}$$

where $Z_0$ is the characteristic acoustic impedance, $N \cdot s/m^3$, $\rho$ is the density of the medium, $kg/m^3$; and c is the longitudinal wave speed or sound speed, m/s. The longitudinal wave speed is the reciprocal of the measured transit time, and so the acoustic impendence can be directly related to transit time and/or acoustic velocity.

The use of acoustic impedance normalizes results with respect to the density of the medium through which the acoustic signal passes. In the case of drilling fluid, the density is the main parameter that must be measured and controlled, and so acoustic impedance allows a direct correlation with density.

Taking the example where a share of reference time is used, a transit time ratio is calculated according to Equation 7 as follows:

$$\Delta TTs_i \frac{\Delta TT_i}{\Delta TT_{max}} \quad \text{(Eq. 7)}$$

where $\Delta TTs_i$ is a transit time ratio and $\Delta TT_i$ is the difference between a measured value and a minimal measured value (time/unit distance) as shown in Equation 8:

$$\Delta TT_i = TT_i - TT_{min} \quad \text{(Eq. 8)}$$

where $TT_i$ is a measured value and $TT_{min}$ is a minimal measured value (time/unit distance).

$\Delta TT_{max}$ is obtained according to Equation 9 as follows:

$$\Delta TT_{max} = TT_{max} - TT_{min} \quad \text{(Eq. 69)}$$

where $TT_{max}$ is the maximum measured value (time/unit distance).

Figure 8:
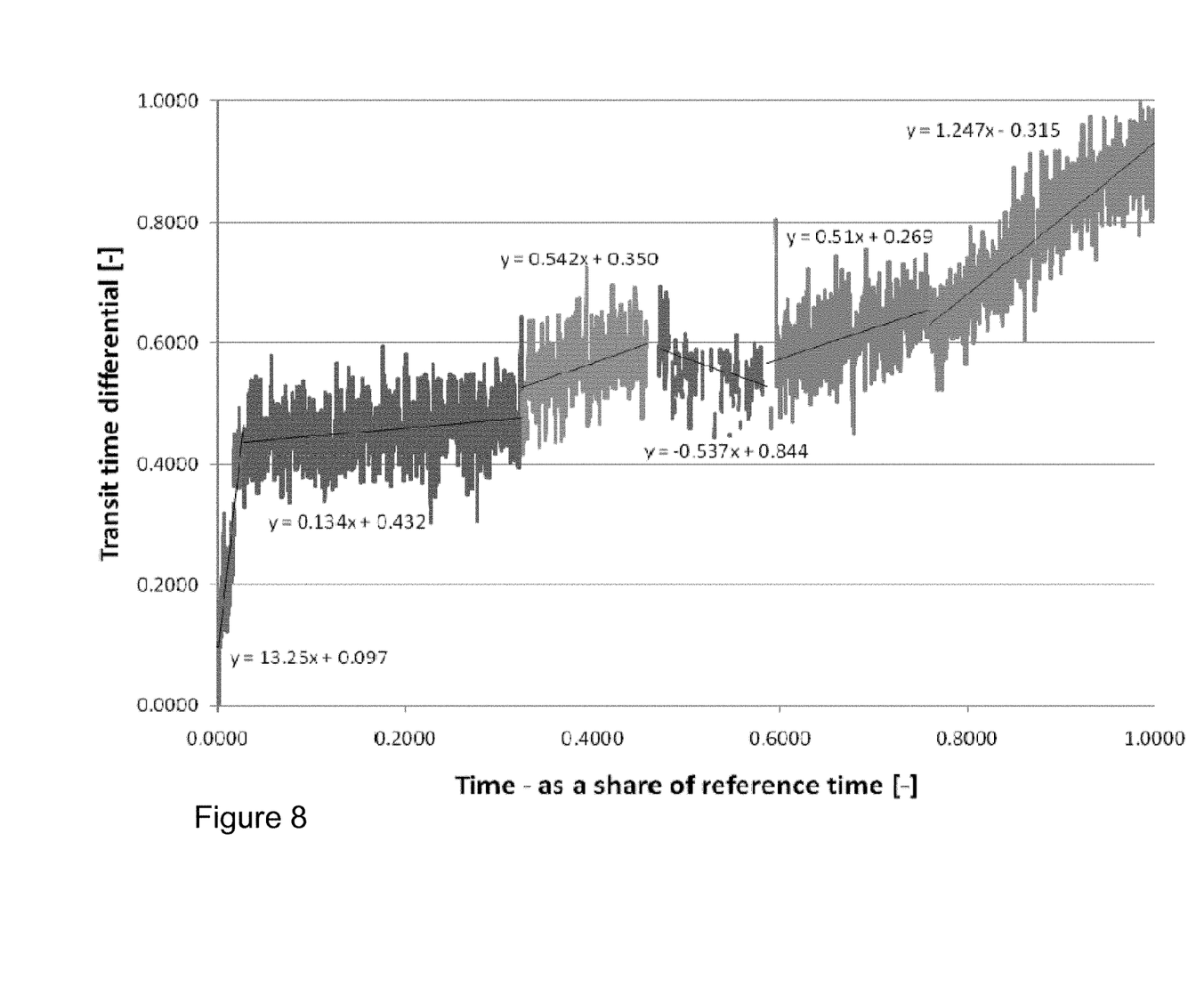
FIG. 8 is a graph showing a transit time differential against the time as a share of reference time.

The results of the calculations performed using Equations 3 and 7 to 9, were used to prepare a graph shown in FIG. 8, showing the transit time differential against the time as a share of reference time. However, note that similar calculations could be made using a calculated share of reference acoustic velocity or a share of acoustic impedance as described above.

In the example of FIG. 8, a gradient has been calculated in different regions of the graph. As mentioned above, the gradient is indicative of rate of settling. The angle of inclination ($\alpha$) for each region can be used as a settling velocity indicator.

In order to compare $\alpha$ values calculated for different test samples, compliance in test time is needed. Each test for which $\alpha$ is calculated needs to be run for the same amount of time in order to be able to use the values in a reference database.

Figure 9:
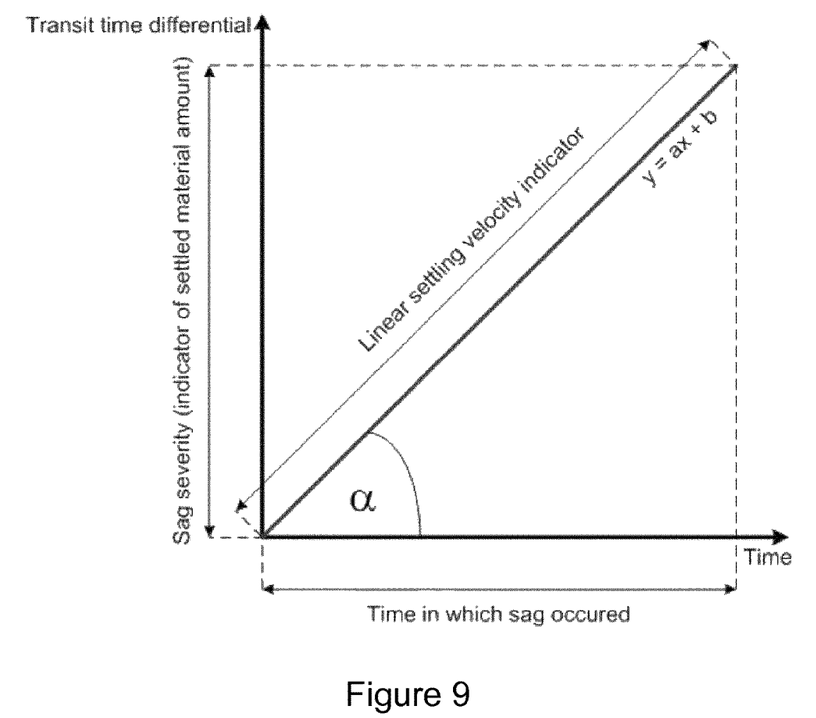
FIG. 9 illustrates schematically a relationship between gradient of transit time differential against the time as a share of reference time, the time in which sag occurred and sag severity.

Settling (sag) severity may be expressed in units of time/distance (or depth) and so cannot be directly correlated to particle settling velocity. FIG. 9 shows how $\alpha$, the time in which sag occurred and the sag severity are related.

An empirical correlation between sag severity and $\alpha$ may be used to predict the probability of sag occurrence in a particular drilling fluid system by obtaining a value for $\alpha$ using a test performed in the field.

$$\tan(\alpha) = \frac{\text{sag severity}}{\text{Time in which sag occurred}} \quad \text{(Eq. 10)}$$

As can be seen from Equation 10, $\tan(\alpha)$ can be expressed as a simple relation between sag severity (indicator of settled material amount) and time in which sag occurred. $\tan(\alpha)$ is also equal to linear function gradient coefficient a. From a chart such as that shown in FIG. 6, the gradient of the slope can easily be correlated to a sag severity and settling time. $\alpha$ can therefore be directly used as a factor to indicate settling velocity.

The results of settling velocity indicator ($\alpha$) calculation for the sample shown in FIGS. 6, 7 and 8 are shown in Table 1 below:

TABLE 1

| Region of graph in FIG. 8 | Equation | tan α |
|---|---|---|
| 1 | y = 13.25x + 0.097 | 13.25 |
| 2 | y = 0.134x + 0.432 | 0.1348 |
| 3 | y = 0.542x + 0.350 | 0.5425 |
| 4 | y = 0.537x + 0.844 | −0.5374 |
| 5 | y = 0.51x + 0.269 | 0.51 |
| 6 | y = 1.247x + 0.315 | 1.2477 |

Various modifications and improvements may be made without departing from the scope of the invention herein described.

The invention claimed is:

1. A method of measuring a rate of settling of a first phase in a second fluid phase of a mixture, the method comprising:
 a. containing the mixture in a chamber;
 b. agitating the mixture using a mixing paddle;
 c. repeatedly passing an acoustic wave vertically through the mixture from a transmitting acoustic transducer at one side of the chamber to a receiving acoustic transducer at an opposite side of the chamber in a direction of settling of particles of the mixture under influence of gravity toward a bottom of the chamber;

d. measuring a transit time for each acoustic wave to traverse the mixture from the transmitting acoustic transducer to the receiving acoustic transducer; and e. determining the rate of settling of said first phase on the bottom of the chamber using a change in the transit times of the acoustic waves wherein the determined rate of settling of said first phase on the bottom of the chamber reflects a relation between settling severity and time in which settling occurs.

2. The method of claim 1, wherein the step of estimating the rate of settling includes comparing the measured transit time with known transit times for a similar mixture under similar conditions to estimate a rate of settling of the first phase in the second fluid phase.

3. The method of claim 1, wherein the step of estimating the rate of settling includes correlating the change in the transit times with the rate of settling according to a correlation relationship derived from historical empirical test results or observations.

4. The method of claim 1, including the steps of estimating values of acoustic impedance of the mixture from the measured transit times, and determining the rate of settling using the values of acoustic impedance.

5. The method of claim 1, further comprising including the step of controlling any of temperature and pressure of the mixture.

6. The method of claim 1, wherein the first phase comprises insoluble solid particles, and the estimate of the rate of settling is used as an estimate of settling of solid particles in the second fluid phase.

7. The method of claim 1, wherein the mixture is a saline mixture, wherein the first phase comprises a salt insoluble in or precipitated from the second fluid phase, wherein the rate of settling of the salt is used as an estimate of salinity or salt saturation.

8. The method of claim 1, further comprising performing steps a, b and c in real time during a drilling operation.

9. The method of claim 1, further comprising the step of:
before the step of repeatedly passing an acoustic wave vertically through the mixture, ceasing agitation of the mixture.

10. The method of claim 1, including the steps of measuring amplitude for each of the acoustic waves, and determining the rate of settling using a change in the amplitudes.

11. The method of claim 10, including comparing the measured amplitude with a reference amplitude to determine an amplitude attenuation for each of the acoustic waves, and determining the rate of settling using a change in the attenuation of amplitudes.

12. The method of claim 1, wherein the mixture comprises an emulsion, wherein the first phase comprises a fluid phase that is immiscible in the second fluid phase.

13. The method of claim 12, wherein the mixture includes a third phase comprising insoluble solid particles.

14. An apparatus for measuring a rate of settling of a first phase in a second fluid phase of a mixture, the apparatus comprising:
a chamber arranged to receive a sample of the mixture;
a mixing paddle arranged to agitate the sample of the mixture;
a source of acoustic waves at one side of the chamber arranged to repeatedly pass acoustic waves vertically through the mixture in a direction of settling of particles of the mixture under influence of gravity toward a bottom of the chamber;
a sensor at an opposite side of the chamber for detecting the acoustic waves; and
a processor configured to determine a transit time for each acoustic wave to traverse the mixture, and determine the rate of settling on the bottom of the chamber using the change in the transit times of the acoustic waves wherein the determined rate of settling of said first phase on the bottom of the chamber reflects a relation between settling severity and time in which settling occurs.

15. The apparatus of claim 14, wherein the processor is configured to process measured times for determining the rate of settling.

16. The apparatus of claim 14, wherein the sensor is arranged to detect an amplitude for each acoustic wave, and the processor determines the rate of settling using the detected amplitudes.

17. The apparatus of claim 14, wherein the processor is further configured to compare the measured transit time with known transit times for a similar mixture under similar conditions to estimate a rate of settling of the first phase in the second fluid phase.

18. The apparatus of claim 17, further comprising a data base of previously obtained data, wherein the processor compares the measured transit time with known transit times for a similar mixture under similar conditions by using the database of previously obtained data.

19. The apparatus of claim 14, wherein the chamber has a transparent window for viewing the mixture.

20. The apparatus of claim 19, wherein the chamber has a back light for illuminating the mixture contained in the chamber for facilitating viewing.

21. The apparatus of claim 14, operable to perform the method of measuring a rate of settling of a first phase in a second fluid phase of a mixture, the method comprising:
a. containing the mixture in a chamber;
b. agitating the mixture using the mixing paddle;
c. repeatedly passing an acoustic wave vertically through the mixture;
d. measuring a transit time for each acoustic wave to traverse the mixture; and
e. determining the rate of settling using a change in the transit times of the acoustic waves.

\* \* \* \* \*